(12) United States Patent
Arcand et al.

(10) Patent No.: US 8,435,261 B2
(45) Date of Patent: May 7, 2013

(54) TREATMENT AND PLACEMENT DEVICE FOR SINUSITIS APPLICATIONS

(75) Inventors: Benjamin Arcand, Minneapolis, MN (US); Joseph E. Hale, Maplewood, MN (US); Nikhil Murdeshwar, Maple Grove, MN (US); Bryan Rolfes, St. Paul, MN (US)

(73) Assignee: Regents of the University of Minnesota, St. Paul ( * ) Notice: Subject to any disclaimer, the term of this patent is extended or adjusted under 35 U.S.C. 154(b) by 168 days.

(21) Appl. No.: 12/837,256

(22) Filed: Jul. 15, 2010

(65) Prior Publication Data

US 2011/0029007 A1 Feb. 3, 2011

Related U.S. Application Data

(60) Provisional application No. 61/225,632, filed on Jul. 15, 2009.

(51) Int. Cl.
*A61M 29/00* (2006.01)
*A61M 5/178* (2006.01)
*A61M 5/32* (2006.01)
*A61M 25/00* (2006.01)

(52) U.S. Cl.
USPC ........ 606/199; 623/10; 604/164.01; 604/264; 604/272

(58) Field of Classification Search .................... 623/10; 604/96.01, 101.01, 159–162, 164.01, 164.02, 604/166.01, 171, 194, 264, 272, 506, 508, 604/509, 510, 514
See application file for complete search history.

(56) References Cited

U.S. PATENT DOCUMENTS 4,737,141 A 4/1988 Spits
4,931,059 A 6/1990 Markham
(Continued)

FOREIGN PATENT DOCUMENTS

WO WO-2006/034008 A2 3/2006
WO WO-2008/008389 A2 1/2008
(Continued)

OTHER PUBLICATIONS

"Internatonal Application Serial No. PCT/US2010/042170, International Preliminary Report on Patentability mailed Jan. 26, 2012", 7 pgs.

(Continued)

*Primary Examiner* — David Isabella
*Assistant Examiner* — Yashita Sharma
(74) *Attorney, Agent, or Firm* — Schwegman, Lundberg & Woessner, P.A.

(57) ABSTRACT

Devices, methods and kits which, when installed or used, access, aspire, dilate, insufflate, drain or deliver fluid medicaments to, or place a patency device within a sinus area, such as a maxillary sinus or a maxillary sinus ostium. The device can include a hollow catheter and probe, and can be configured to permit gradual and incremental probe extension. The device can be constructed to enhance the precision and maneuverability within the nasal and sinus passageways, while also accommodating the natural anatomical geometry of a targeted paranasal treatment site. For example, the present treatment and placement device can accomplish access to the maxillary sinus ostium by utilizing an uncinate process to guide a probe tip into the ostium in a retrograde manner. The probe can be slidably, bi-directionally or co-axially positioned within the catheter. A distal portion of the probe can be biased away from a longitudinal axis of the catheter.

11 Claims, 9 Drawing Sheets

U.S. PATENT DOCUMENTS

| | | | |
|---|---|---|---|
| 4,964,850 | A | 10/1990 | Bouton et al. |
| 5,139,502 | A | 8/1992 | Berg et al. |
| 5,169,386 | A | 12/1992 | Becker et al. |
| 5,246,455 | A | 9/1993 | Shikani |
| 5,336,163 | A | 8/1994 | DeMane et al. |
| 5,492,538 | A | 2/1996 | Johlin, Jr. |
| 5,538,504 | A | 7/1996 | Linden et al. |
| 5,584,827 | A | 12/1996 | Korteweg et al. |
| 5,599,284 | A | 2/1997 | Shea |
| 5,599,294 | A | 2/1997 | Edwards et al. |
| 5,599,304 | A | 2/1997 | Shaari |
| 5,601,594 | A | 2/1997 | Best |
| 5,693,065 | A | 12/1997 | Rains, III |
| 5,758,656 | A | 6/1998 | Schroeder |
| 5,897,521 | A | 4/1999 | Lavigne |
| 6,027,478 | A | 2/2000 | Katz |
| 6,283,951 | B1 | 9/2001 | Flaherty et al. |
| 6,607,546 | B1 | 8/2003 | Murken |
| 6,613,081 | B2 | 9/2003 | Kim et al. |
| 6,863,684 | B2 | 3/2005 | Kim et al. |
| 7,169,163 | B2 | 1/2007 | Becker |
| 7,235,099 | B1 | 6/2007 | Duncavage et al. |
| 7,361,168 | B2 | 4/2008 | Makower et al. |
| 7,387,618 | B2 | 6/2008 | Ishii et al. |
| 7,410,480 | B2 | 8/2008 | Muni et al. |
| 7,455,688 | B2 | 11/2008 | Furst et al. |
| 7,500,971 | B2 | 3/2009 | Chang et al. |
| 7,544,192 | B2 | 6/2009 | Eaton et al. |
| 7,559,925 | B2 | 7/2009 | Goldfarb et al. |
| 7,597,901 | B2 | 10/2009 | Clarot et al. |
| 7,645,272 | B2 | 1/2010 | Chang et al. |
| 7,654,997 | B2 | 2/2010 | Makower et al. |
| 7,655,243 | B2 | 2/2010 | Deem et al. |
| 7,662,141 | B2 | 2/2010 | Eaton et al. |
| 7,662,142 | B2 | 2/2010 | Eaton et al. |
| 7,678,099 | B2 | 3/2010 | Ressemann et al. |
| 8,025,635 | B2 | 9/2011 | Eaton et al. |
| 2002/0049414 | A1 | 4/2002 | Nobles et al. |
| 2004/0064083 | A1 | 4/2004 | Becker |
| 2004/0064150 | A1 | 4/2004 | Becker |
| 2004/0116958 | A1 | 6/2004 | Gopferich et al. |
| 2005/0240147 | A1 | 10/2005 | Makower et al. |
| 2006/0004286 | A1 | 1/2006 | Chang et al. |
| 2006/0004323 | A1 | 1/2006 | Chang et al. |
| 2006/0063973 | A1 | 3/2006 | Makower et al. |
| 2006/0095066 | A1 | 5/2006 | Chang |
| 2006/0129223 | A1 | 6/2006 | Jabbour et al. |
| 2006/0149310 | A1 | 7/2006 | Becker |
| 2006/0210605 | A1 | 9/2006 | Chang et al. |
| 2006/0249161 | A1* | 11/2006 | Waters et al. ............ 128/207.18 |
| 2007/0005094 | A1 | 1/2007 | Eaton et al. |
| 2007/0021730 | A1 | 1/2007 | Flaherty et al. |
| 2007/0073269 | A1 | 3/2007 | Becker |
| 2007/0123924 | A1 | 5/2007 | Becker |
| 2007/0129751 | A1 | 6/2007 | Muni et al. |
| 2007/0135789 | A1 | 6/2007 | Chang et al. |
| 2007/0167682 | A1 | 7/2007 | Goldfarb et al. |
| 2007/0179518 | A1 | 8/2007 | Becker |
| 2007/0208301 | A1 | 9/2007 | Evard et al. |
| 2007/0249896 | A1 | 10/2007 | Goldfarb et al. |
| 2007/0269385 | A1 | 11/2007 | Yun et al. |
| 2007/0293726 | A1 | 12/2007 | Goldfarb et al. |
| 2007/0293727 | A1 | 12/2007 | Goldfarb et al. |
| 2007/0293946 | A1 | 12/2007 | Gonzales et al. |
| 2008/0015472 | A1 | 1/2008 | Ressemann et al. |
| 2008/0015497 | A1 | 1/2008 | Keith et al. |
| 2008/0015544 | A1 | 1/2008 | Keith et al. |
| 2008/0015626 | A1 | 1/2008 | Keith et al. |
| 2008/0033353 | A1 | 2/2008 | Truitt et al. |
| 2008/0097154 | A1 | 4/2008 | Makower et al. |
| 2008/0097295 | A1 | 4/2008 | Makower et al. |
| 2008/0097400 | A1 | 4/2008 | Chang et al. |
| 2008/0097514 | A1 | 4/2008 | Chang et al. |
| 2008/0097515 | A1 | 4/2008 | Chang et al. |
| 2008/0097516 | A1 | 4/2008 | Chang et al. |
| 2008/0103361 | A1 | 5/2008 | Makower et al. |
| 2008/0103521 | A1 | 5/2008 | Makower et al. |
| 2008/0119693 | A1 | 5/2008 | Makower et al. |
| 2008/0125626 | A1 | 5/2008 | Chang et al. |
| 2008/0125720 | A1 | 5/2008 | Kim et al. |
| 2008/0132938 | A1 | 6/2008 | Chang et al. |
| 2008/0154237 | A1 | 6/2008 | Chang et al. |
| 2008/0154250 | A1 | 6/2008 | Makower et al. |
| 2008/0172033 | A1 | 7/2008 | Keith et al. |
| 2008/0195041 | A1 | 8/2008 | Goldfarb et al. |
| 2008/0208242 | A1 | 8/2008 | Becker |
| 2008/0208243 | A1 | 8/2008 | Becker |
| 2008/0215082 | A1 | 9/2008 | Becker |
| 2008/0215083 | A1 | 9/2008 | Becker |
| 2008/0228085 | A1 | 9/2008 | Jenkins et al. |
| 2008/0234720 | A1 | 9/2008 | Chang et al. |
| 2008/0243140 | A1 | 10/2008 | Gopferich et al. |
| 2008/0249500 | A1 | 10/2008 | Keith et al. |
| 2008/0262468 | A1 | 10/2008 | Clifford et al. |
| 2008/0262509 | A1 | 10/2008 | Clifford et al. |
| 2008/0275483 | A1 | 11/2008 | Makower et al. |
| 2008/0281300 | A1 | 11/2008 | Morriss |
| 2008/0281349 | A2 | 11/2008 | Becker |
| 2008/0287908 | A1 | 11/2008 | Muni et al. |
| 2008/0294255 | A1 | 11/2008 | Gonzales |
| 2008/0319424 | A1 | 12/2008 | Muni et al. |
| 2009/0005763 | A1 | 1/2009 | Makower et al. |
| 2009/0017090 | A1 | 1/2009 | Arensdorf |
| 2009/0028923 | A1 | 1/2009 | Muni et al. |
| 2009/0030274 | A1 | 1/2009 | Goldfarb et al. |
| 2009/0036968 | A1 | 2/2009 | Hepworth et al. |
| 2009/0047326 | A1 | 2/2009 | Eaton et al. |
| 2009/0047327 | A1 | 2/2009 | Eaton et al. |
| 2009/0093823 | A1 | 4/2009 | Chang et al. |
| 2009/0125046 | A1 | 5/2009 | Becker |
| 2009/0171301 | A1 | 7/2009 | Becker |
| 2009/0177272 | A1 | 7/2009 | Abbate et al. |
| 2009/0187098 | A1 | 7/2009 | Makower et al. |
| 2009/0198179 | A1 | 8/2009 | Abbate et al. |
| 2009/0198216 | A1 | 8/2009 | Muni et al. |
| 2009/0216196 | A1 | 8/2009 | Drontle et al. |
| 2009/0220571 | A1 | 9/2009 | Eaton et al. |
| 2009/0221988 | A1 | 9/2009 | Ressemann et al. |
| 2009/0227945 | A1 | 9/2009 | Eaton et al. |
| 2009/0238859 | A1 | 9/2009 | Eaton et al. |
| 2009/0240112 | A1 | 9/2009 | Goldfarb et al. |
| 2009/0306624 | A1 | 12/2009 | Arensdorf et al. |
| 2009/0312745 | A1 | 12/2009 | Goldfarb et al. |
| 2010/0030031 | A1 | 2/2010 | Goldfarb et al. |
| 2010/0030113 | A1 | 2/2010 | Morriss et al. |
| 2010/0042046 | A1 | 2/2010 | Chang et al. |
| 2010/0043197 | A1 | 2/2010 | Abbate et al. |
| 2011/0015612 | A1 | 1/2011 | Arcand et al. |

FOREIGN PATENT DOCUMENTS

| | | |
|---|---|---|
| WO | WO-2009/079418 A2 | 6/2009 |
| WO | WO-2011/008981 A1 | 1/2011 |
| WO | WO-2011/008987 A2 | 1/2011 |

OTHER PUBLICATIONS

"International Application Serial No. PCT/US2010/042177, International Preliminary Report on Patentability mailed Jan. 26, 2012", 8 pgs.

"Management of Allergic and Nonallergic Rhinitis", *AHQR Publication 02:E023, Evidence Report/Technology Assessment No. 54*, U.S. Department of Health and Human Services. Agency for Healthcare Research and Quality, Boston, MA, (May 2002), 195 pgs.

Bender, B. G., "Cognitive effects of allergic rhinitis and its treatment", *Immunology and Allergy Clinics of North America*, 25(2), (2005), 301-312.

Ray, N. F., et al., "Direct expenditures for the treatment of allergic rhinoconjunctivitis in 1996, including the contributions of related airway illnesses", *The Journal of Allergy and Clinical Immunology*, 103(3), (1999), 401-407.

Schatz, M., et al., "The burden of rhinitis in a managed care organization", *Ann Allergy Asthma Immunol.*, 101(3), (2008), 240-247.

Settipane, R. A., "Demographics and epidemiology of allergic and nonallergic rhinitis", *Allergy and Asthma Proceedings*, 22(4), (2001), 185-189.

Sly, R. M., "Changing prevalence of allergic rhinitis and asthma", *Ann. Allergy Asthma Immunology*, 82(3), (1999), 233-248.

Torrance, G. W., "Preferences for Health Outcomes and Cost-Utility Analysis", *The American Journal of Managed Care*, 3(Suppl.), (May 1997), S8-S20.

Von Mutius, E., et al., "Increasing prevalence of hay fever and atopy among children in Leipzig, East Germany", *Lancet*, 351(9106), (1998), 862-866.

Woods, L., et al., "The importance of rhinitis on sleep, daytime somnolence, productivity and fatigue", *Curr. Opin. Pulm. Med.*, 12(6), (2006), 390-396.

"International Application Serial No. PCT/US2010/042170, International Search Report mailed Oct. 1, 2010", 4 pgs.

"International Application Serial No. PCT/US2010/042170, Written Opinion mailed Oct. 1, 2010", 6 pgs.

"International Application Serial No. PCT/US2010/042177, International Search Report mailed Mar. 9, 2011", 5 pgs.

"International Application Serial No. PCT/US2010/042177, Written Opinion mailed Mar. 9, 2011", 7 pgs.

"U.S. Appl. No. 12/837,224, Non Final Office Action mailed Mar. 9, 2012", 13 pgs.

"U.S. Appl. No. 12/837,224, Response filed Jun. 6, 2012 to Non Final Office Action mailed Mar. 9, 2012", 14 pgs.

\* cited by examiner

TREATMENT AND PLACEMENT DEVICE FOR SINUSITIS APPLICATIONS

CLAIM OF PRIORITY

This non-provisional patent application claims the benefit of priority under 35 U.S.C. §119(e) to U.S. Provisional Patent Application Ser. No. 61/225,632, entitled "DEVICE FOR MAXILLARY SINUS OSTIUM,", filed on Jul. 15, 2009, which is hereby incorporated by reference in its entirety.

TECHNICAL FIELD

This patent document pertains generally to devices, methods and kits to treat sinusitis. More particularly, but not by way of limitation, this patent document pertains to treatment and placement devices, methods and kits which, when installed or used, dilate, maintain or otherwise treat sinus ostia.

BACKGROUND

"Sinusitis" refers to inflammation of one or more nasal sinus cavities, which are moist, hollow spaces in the bones of the skull. Sinusitis affects millions of people each year. According to the National Ambulatory Medical Care Survey (NAMCS), approximately 14% of adults report having at least one yearly episode of sinusitis. Further, sinusitis is believed to be one of the top five most common diagnoses for which antibiotics are prescribed.

There are four pairs of sinuses: frontal, maxillary, ethmoid, and sphenoid. The sinuses are located behind the eyebrows, cheekbones, and nose. The sinuses help moisten and warm air that is filtered by the nose, serving to protect the lungs. The sinus cavities, nose, and lungs are lined with mucous membranes, which protect the airways by trapping irritants that are inhaled. Tiny hair-like filaments called cilia are in constant movement and sweep mucus and the trapped irritants out of the airways and nasal passages. In each of the sinuses, the mucus drains out of a tiny opening called the ostium.

The ostium of any sinus cavity can get plugged. When this blockage prevents the flow of mucus, the pressure builds up, leading to sinusitis typified by inflammation and pain. If the blocked sinus becomes infected with bacteria, the sinus becomes even more inflamed and painful. Symptoms of sinusitis can include, among other things, facial pain or pressure, discolored mucus, a diminished sense of smell, cough, headache, bad breath, fever, toothache, pressure in the ears and fatigue.

OVERVIEW

The present inventors have recognized, among other things, a need for sinus specific treatment devices that can effectuate clinical-based therapy, and can comfortably accommodate the natural nasal and sinus geometries in maneuvering and placement of sinus ostium patency devices.

The present treatment and placement device is configured to access, aspire, dilate, insufflate, drain or deliver fluid medicaments to, or place a patency device within a sinus area, such as a maxillary sinus area, via an associated sinus ostium. The present inventors have discovered that a device can be constructed, which enhances the precision and maneuverability within the nasal and sinus passageways, while also accommodating the natural anatomical geometry of a target treatment site, such as the maxillary sinus. Although accessing the maxillary sinus can be achieved through a nostril and associated nasal cavity, such an approach is complicated by an intermediate or middle concha that projects over the maxillary sinus ostium, as well as, an uncinate process that obstructs the approach in an anterior toward posterior direction. The present treatment and placement device accomplishes access to the maxillary sinus ostium, for example, by utilizing the uncinate process to guide a moveable probe tip into the ostium in a retrograde, posterior toward anterior manner.

To better illustrate the devices, methods and kits disclosed herein, a non-limiting list of examples is provided here:

In Example 1, a device for accessing a sinus ostium comprises a catheter extending from a proximal end to a distal end, and including a longitudinally-extending lumen and an intersecting side portal; and a probe at least partially nested within the longitudinally-extending lumen, a portion of the probe movable within the lumen such that a probe tip is advanceable out of the intersecting side portal, wherein the intersecting side portal is located proximal to the distal end of the catheter.

In Example 2, the device of Example 1 is optionally configured such that the probe includes a first portion and a second portion separated by a preformed bend, the first portion extending from a probe proximal end to the preformed bend and the second portion extending from the preformed bend in a direction toward the probe proximal end.

In Example 3, the device of any one or any combination of Examples 1 and 2 is optionally configured such that the preformed bend forms an angle between about 90 degrees and about 180 degrees relative to an axis defined by the catheter distal end.

In Example 4, the device of Example 2 is optionally configured such that the probe tip advances out of the intersecting side portal at an angle less than 90 degrees relative to an axis defined by the first portion of the probe at a superimposed position of the probe tip. In some examples, the advancing angle is between about 15 degrees and about 75 degrees, and more preferably, between about 20 degrees and about 60 degrees.

In Example 5, the device of any one or any combination of Examples 1-4 is optionally configured such that the probe tip is configured to advance out of the intersecting side portal in a posterior to anterior direction.

In Example 6, the device of any one or any combination of Examples 1-5 is optionally configured such that a distal portion of the catheter includes an arcuate shape and a groove, located proximal to the intersecting side portal, to assist probe tip advancement and support.

In Example 7, the device of any one or any combination of Examples 1-6 is optionally configured such that the probe is moveable within the longitudinally-extending lumen without movement of the catheter.

In Example 8, the device of any one or any combination of Examples 1-7 is optionally configured such that the probe includes a tubular configuration and one or more openings at or near the probe tip.

In Example 9, the device of Example 8 optionally further comprises an inflatable or expansible element coupled to the probe at or near the probe tip, such that the one or more openings are in communication with an interior of the inflatable or expansible element.

In Example 10, the device of any one or any combination of Examples 1-9 is optionally configured such that the catheter includes a combination of a semi-rigid internal material and a softer, more pliable exterior material.

In Example 11, a method comprises advancing a catheter and a probe, the probe including a double-backed portion nested inside the catheter, within a middle meatus between an intermediate concha and an inferior concha; and accessing a maxillary sinus ostium using the double-backed portion of the probe, including actuating a probe tip in a posterior to anterior direction.

In Example 12, the method of Example 11 is optionally configured such that actuating the probe tip and accessing the maxillary sinus ostium includes using an uncinate process to aid in guiding the probe tip into the maxillary sinus ostium.

In Example 13, the method of any one or any combination of Examples 11 or 12 is optionally configured such that actuating the probe tip includes linearly moving an actuation mechanism, coupled to the probe, in a proximal direction.

In Example 14, the method of any one or any combination of Examples 11-13 is optionally configured such that actuating the probe tip includes moving the catheter in an anterior to posterior direction.

In Example 15, the method of any one or any combination of Examples 11-14 is optionally configured such that actuating the probe tip includes allowing a preformed probe tip to bias away from a longitudinal axis of the catheter.

In Example 16, the method of any one or any combination of Examples 11-15 is optionally configured such that advancing the catheter and probe, the probe nested inside the catheter, includes advancing a sinus ostium patency device removably coupled to a portion of the catheter or probe.

In Example 17, the method of any one or any combination of Examples 11-16 optionally further comprises performing one or more of: aspiring, dilating, insufflating, draining, delivering fluid medicaments to, or placing a patency device within the maxillary sinus ostium or maxillary sinus cavity.

In Example 18, the method of Example 17 is optionally configured such that aspiring, dilating, insufflating, draining or delivering fluid medicaments to the maxillary sinus ostium or maxillary sinus cavity includes using one or more openings at or near the probe tip and a fluid container in communication with a probe proximal end.

In Example 19, the method of Example 17 is optionally configured such that dilating the maxillary sinus ostium includes inflating a balloon coupled to the probe at or near the probe tip.

In Example 20, the method of Example 19 optionally further comprises placing the patency device within the dilated maxillary sinus ostium.

In Example 21, the method of any one or any combination of Examples 11-20 is optionally configured such that accessing the maxillary sinus ostium using the probe includes using tactile feedback.

In Example 22, a kit comprises a device according to any one or any combination of Examples 1-10; and a set of instructions for using the device to treat an ostium associated with a maxillary sinus.

In Example 23, the kit of Example 22 optionally further comprises a sinus ostium patency device, the patency device including a partially open cross-sectional configuration for maintaining a track of uncovered cilia within the ostium.

In Example 24, the device, method or kit of any one or any combination of Examples 1-23 is optionally configured such that all elements or options recited are available to use or select from.

These and other examples, advantages, and features of the present treatment and placement devices, methods and kits will be set forth in part in following Detailed Description. This Overview is intended to provide non-limiting examples of the present subject matter—it is not intended to provide an exclusive or exhaustive explanation. The Detailed Description is included to provide further information about the present treatment and placement devices, methods and kits.

BRIEF DESCRIPTION OF THE DRAWINGS

In the drawings, like numerals can be used to describe similar components throughout the several views. Like numerals having different letter suffixes can be used to represent different instances of similar components. The drawings illustrate generally, by way of example, but not by way of limitation, various embodiments discussed in the present document.

DETAILED DESCRIPTION

The present invention provides devices, methods and kits for accessing and treating a maxillary sinus ostium and associated maxillary sinus, for example. The device is structured to accommodate natural sinus geometry, including the maxillary sinus and maxillary sinus ostium, in terms of its dimensions, configurations, or operability. In various examples, a distal curvature of the device can be configured for insertion and positioning the distal portion of the device adjacent to the maxillary sinus ostium and within the middle meatus between the intermediate concha and inferior concha. Features of the present device increase the precision of positioning into the maxillary sinus ostium by accounting for the complications associated with the intermediate concha, which projects over the maxillary sinus ostium, and the uncinate process which obstructs the approach in an anterior toward posterior direction. The distal portion of the device can utilize the uncinate process to guide a probe tip into the maxillary sinus ostium. These and other components of the device can be configured to perform a variety of functions within the maxillary sinus ostium or the maxillary sinus cavity, including but not limited to, dilation, insufflation, fluid or medication delivery, drainage, sinus ostium patency device delivery, biopsy and sampling, cutting or ablation, or endoscopic visualization.

Figure 1:
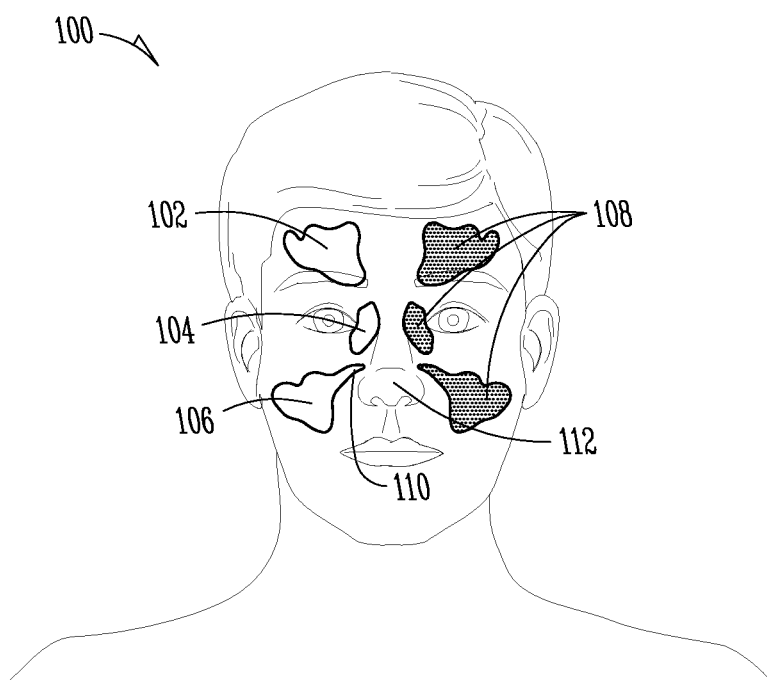
FIG. 1 illustrates an example schematic view of anatomical tissue structures including the maxillary, frontal, and ethmoid sinus cavities, such tissue structures providing a suitable environment in which a treatment and placement device, as constructed in accordance with at least one embodiment, can be used.

To facilitate understanding of the physiology associated with the present treatment and placement devices, methods and kits, FIG. 1 illustrates anatomical tissue structures 100 associated with sinusitis. There are four different pairs of sinuses—the frontal sinuses 102, the ethmoid sinuses 104, the maxillary sinuses 106, and the sphenoid sinuses (located more toward the back of the head than the other sinuses). Normally, sinuses are filled with air, but when sinuses become blocked and filled with fluid, pathogens can grow and cause an infection. In FIG. 1, the sinuses on the (reader's) right side are shown as inflamed, infected and experiencing sinusitis 108.

Sinusitis 108 can be acute or chronic. Acute sinusitis usually lasts for approximately 3 weeks, but can persist for as long as 3 months. Acute sinusitis is usually caused by a viral respiratory infection. Subjects with acute or recurrent acute sinusitis are typically treated with antibiotics or over-the-counter decongestants.

Chronic sinusitis lasts longer than three months and does not respond well to conventional antibiotic treatment. Chronic sinusitis can also be caused by infection, but is more often caused by inflammation and blockage due to allergies or a physical obstruction (e.g., collapsed bone or cartilage structures or foreign objects). Traditionally, chronic sinusitis is treated using Functional Endoscopic Sinus Surgery, commonly known as a FESS procedure. During a traditional FESS procedure, a physician caregiver resects or removes bone and tissue to enlarge a sinus ostium of interest to restore adequate cavity drainage. Removal of bone and tissue can lead to considerable post-operative pain.

A technological concept of the present treatment and placement devices, methods and kits is to open and maintain a blocked maxillary sinus ostium 110 extending between a cavity of the maxillary sinus 106 and a nasal passage 112, for example, to reduce mucus pressure build-up and the resulting pain experience by a subject without removing bone or tissue. Non-removal procedures, by nature, are associated with less healing times and discomfort than invasive removal procedures, and thus, provide advantages over surgical such procedures.

Figure 2A:
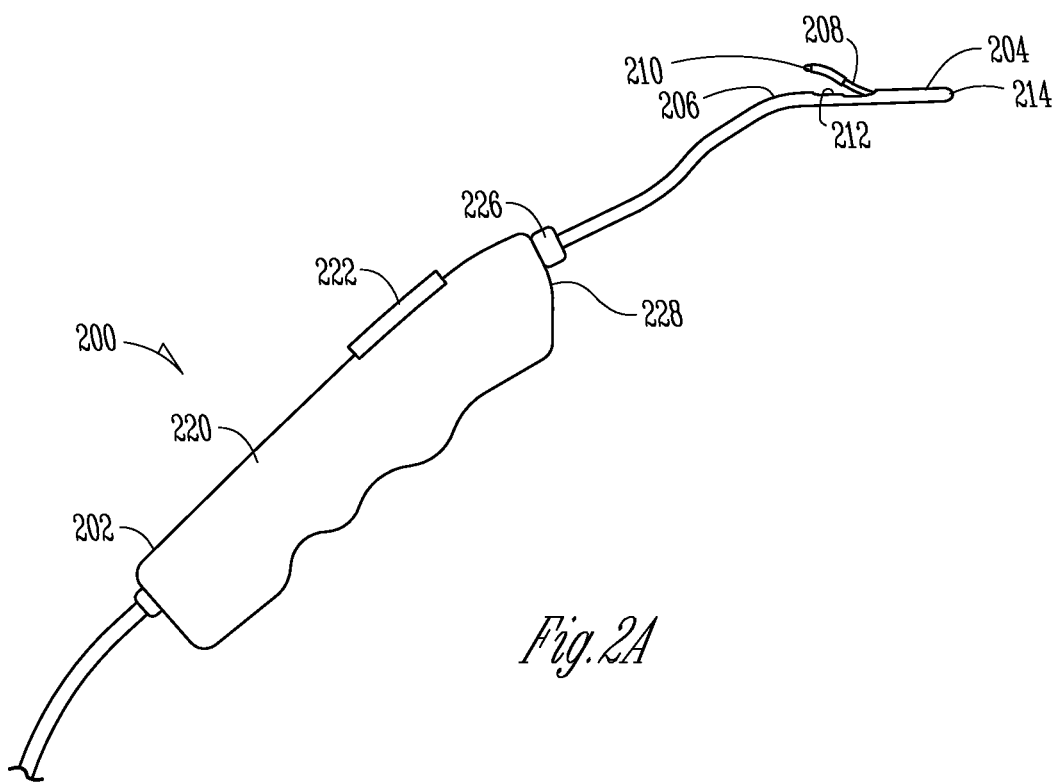
FIG. 2A-2B illustrate schematic and detailed views of an example treatment and placement device, as constructed in accordance with at least one embodiment.
Figure 2B:
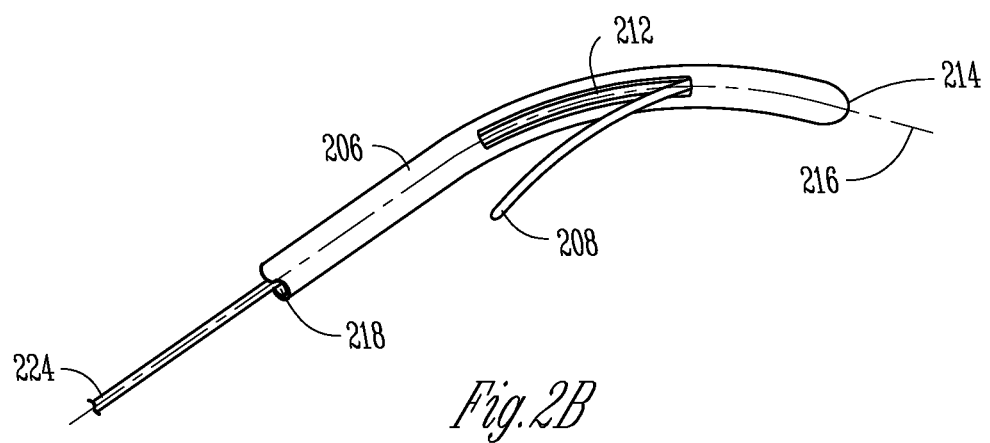

FIGS. 2A and 2B illustrate schematic and detailed views of an example treatment and placement device 200. The treatment and placement device 200 can extend from a first, proximal portion 202 to a second, distal portion 204, and can include a catheter 206 that houses a movable probe 208 (shown in a deployed position). The distal portion 204 of the housing may include an arcuate shape, and at least a portion of the probe is nested within the arcuate shaped housing. The probe 208 can be doubled-backed within the catheter 206 so that its tip 210 faces towards the first portion 202 of the device 200. The probe tip 210 can be enabled through the use of a side or lateral portal 212 in the catheter 206, in lieu of a distal tip 214 portal, and can be configured for delivery of a therapy or a patency implant, or dilation (e.g., via a balloon), among other things. The catheter 206 can have a longitudinal axis 216 and an internal lumen 218. The side or lateral portal 212 can be in communication with the internal lumen 218 and located proximal the distal tip 214 of the catheter 206. In various examples, the second portion 204 of the catheter can include a generally arcuate configuration, as shown in the reoriented illustration of FIG. 2B, to facilitate positioning adjacent to the maxillary sinus ostium 110 (FIG. 1) and within the middle meatus between the intermediate concha and inferior concha.

The probe 208 can be actuated for retrograde movement (i.e., movement toward the first portion 202) without requiring movement of the catheter 206. The movement of the probe 208 relative to the catheter 206 is shown, for example, in FIGS. 4A (nested position) and 4B (deployed position). Advantageously, the probe's 208 ability to be actuated and extend away from the stationary catheter 206 can reduce the need for "poking" to locate an ostium and can increase the precision of ostium access.

A variety of mechanisms can be used to move the probe 208 relative to the catheter 206. As shown in the example of FIG. 2A, the treatment and placement device 200 can include a handle assembly 220 at the first portion 202. The handle assembly 220 can include a handle housing and a manually controllable sliding switch 222. The sliding switch 222 can be mechanically coupled to a proximal end 224 of the probe 208, and a proximal end 226 of the catheter 206 can be fixedly attached to a distal end 228 of the handle assembly 220. In this example, movement of the sliding switch 222 in the proximal direction can correspondingly move a distal tip 210 portion of the probe 208 in the proximal direction. Advantageously, linear movement of the sliding switch 222 or other mechanical mechanism, in combination with a biased outward orientation of the double-packed portion 606 (FIG. 6) of the probe 208, can allow gradual and incremental spacing between the deployed probe portion and the catheter 206 (e.g., when moved proximally, the double-backed portion of the probe 208 is permitted to incrementally extend away from the catheter 206), thereby allowing for precise ostium 110 delivery of a therapy (e.g., medicament), dilation or delivery of an ostium patency implant, among other things. Alternatively, the probe 208 can be deployed by moving the catheter 206 in the distal direction thereby permitting extension of the probe 208 with the linear portion of the probe being stationary relative to sinus position.

The probe 208, catheter 206, or both, can be constructed to perform a variety of functions in addition delivery of a therapy, dilation or delivery of a patency implant. The one or more portions of the probe 208 can be in the form of a solid stylet or access instrument. The probe 208 can be structured for positioning and depositing of a variety of implantable devices into the maxillary sinus ostium 110. The probe 208 can be configured as a hollow tube, and can comprise one or more ports or openings at or near the distal tip 210 for insufflation, infusion or fluid delivery to the ostium 110 or directly into the maxillary sinus 106 (FIG. 1). A variety of fluid medicaments can be applied to a subject patient using the treatment and placement device 200. The distal tip 210 portion of the probe 208 can include an inflatable or expansible element, such as a stent or balloon structure. In some examples, the distal tip 210 portion of the probe 208 can include ultrasonic or electrical components for ablation or cauterization. Additional equipment and components, such as endoscopic visualization equipment or illumination systems, can also be incorporated into the handle assembly 220 or elsewhere.

The catheter 206 can be composed of a semi-rigid, flexible material having structural integrity sufficient to permit positioning within a sinus and maneuvering and operation of the device 200, while permitting yielding and bending in response to encountered anatomical barriers and obstacles within the nasal and sinus passageways. Suitable materials include, but are not limited to, plastics and polymeric materials. Examples of suitable plastics and polymeric materials include, but are not limited to, silastic materials and silicon-based polymers, polyurethane, and the like. In some examples, soft durometer materials are used for the catheter 206 to reduce subject recipient discomfort. In some examples, the catheter 206 can be composed of two different materials, such as the combination of a semi-rigid internal material and a soft, pliable exterior material.

The probe 208 can be composed of semi-rigid, flexible material having sufficient structural integrity to permit operation within the device 200 and insertion into a maxillary sinus ostium 110, for example. Suitable materials include, but are not limited to, plastics and polymeric materials, and metals and metallic alloys. Examples of metals and alloys that can be employed include, but are not limited to, Nitinol, titanium, stainless steel, and the like.

Any part of the treatment and placement device 200 can include a radiopaque marker as either a solid marker attached to a portion of the device or as fine powder mixed with the catheter or probe material during construction. Additional features for the treatment and placement device 200 include: pre-loading of a diagnostic, therapeutic or other active agent; a reservoir (e.g., to store active agent(s)); inclusion of an endoscope of other internal viewing device (e.g., a light-emitting means); coating with a hydrophilic material; configuration for placement within a frontal sinus; a hose for draining and/or rinsing a maxillary sinus; or specimen capturing jaws for removal of a tissue sample (biopsy).

Figure 3A:
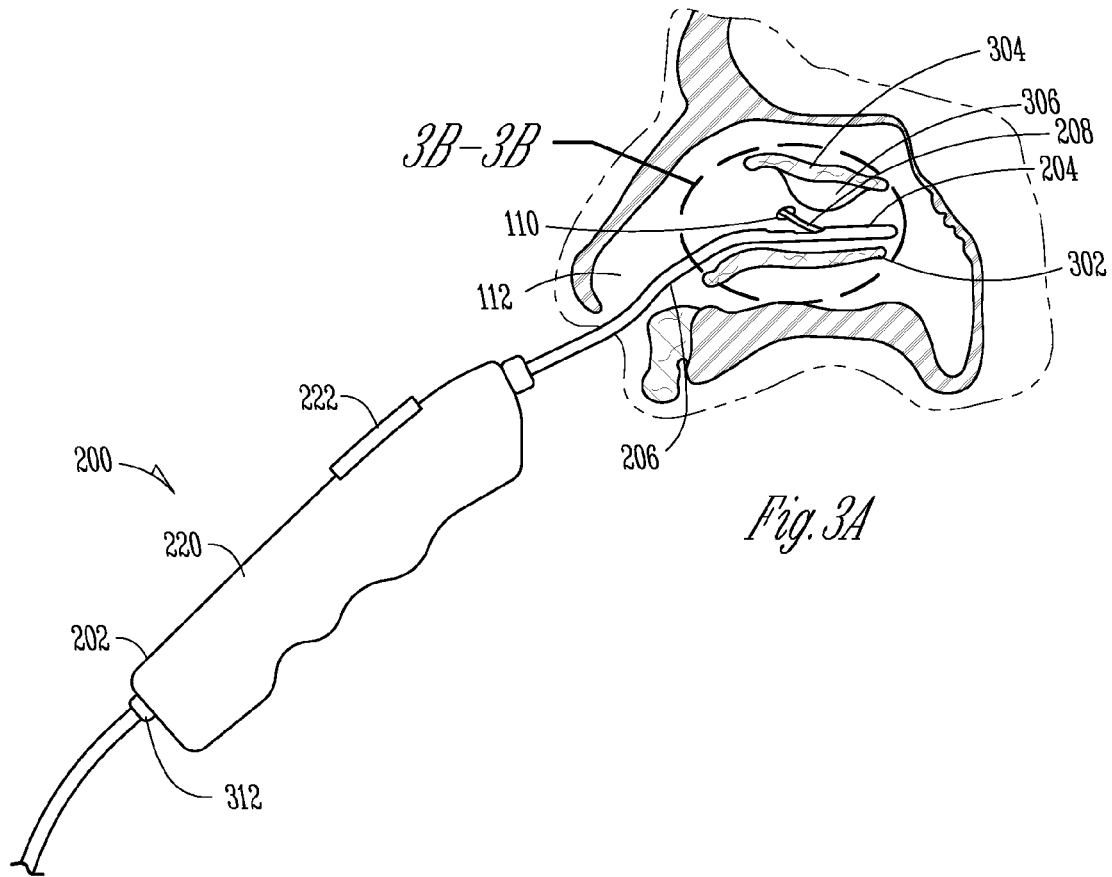
FIGS. 3A-3B illustrate schematic and detailed views of an example treatment and placement device and a patency device positioned within a sinus ostium, the treatment and placement device and the patency device as constructed in accordance with at least one embodiment.
Figure 3B:
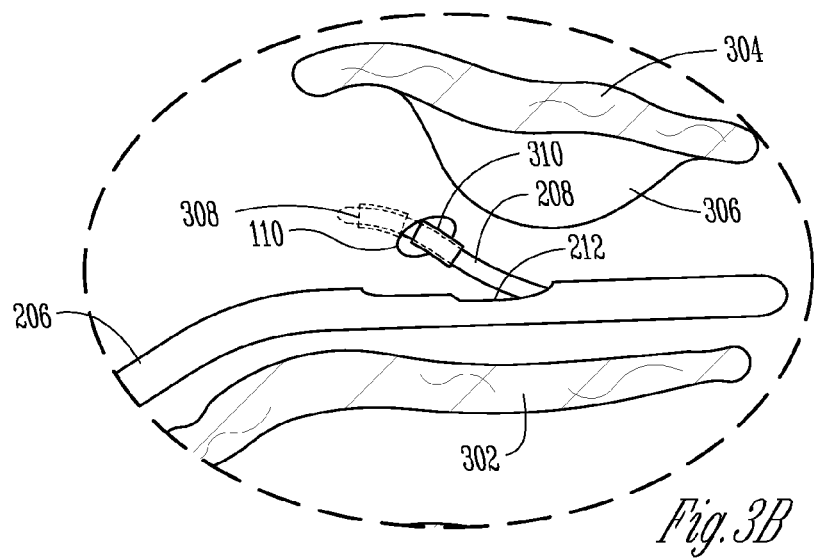

As shown in FIGS. 3A and 3B, a treatment and placement device 200 can be designed to navigate the bony and cartilaginous obstructions within a nasal passageway 112 and access a maxillary sinus ostium 110 for dilation, insufflation, fluid or medication delivery, drainage, sinus ostium patency device delivery, biopsy and sampling, cutting or ablation or endoscopic visualization, among other things, in a retrograde manner. This novel approach is unique and can be enabled through the use of a side or lateral portal instead of a distal portal. Specifically, FIGS. 3A and 3B illustrate a catheter 206 positioned inside the nasal passageway 112 and a probe 208 in a deployed position, partially inserted into the maxillary sinus ostium 110.

The overall catheter 206, or portions thereof, can be shaped to facilitate positioning alongside the sinus ostium 110 by providing an angle configured to enter the nasal passageway 112 and slide within the middle meatus between a middle concha 304 and an inferior concha 302. The probe 208 that exits the catheter 206 via the lateral portal 212 can be shaped so that it bends toward the sinus ostium 110 and uses an uncinate process 306 to aid in advancement into the ostium 110. Location monitoring of the catheter 206 and probe 208 during a procedure can, in some examples, be determined using tactile feedback alone or in combination with an imaging means.

The probe 208 can be separately actuated for retrograde movement without requiring movement of the catheter 206. The first portion 202 of the treatment and placement device 200 can include a handle assembly 220 with a sliding switch or other mechanism 222 to actuate the probe 208 out of, and back into, the catheter 206. A balloon or other dilator 308 can be advanced via actuation of the probe 208 and positioned through a blocked sinus ostium 110. When the balloon or other dilator 308 is inflated (e.g., via a lumen within the probe 208), the fragile bones of the sinus ostium 110 can be permanently or sufficiently moved aside to open up air and mucus flow. Optionally, a sinus ostium patency device 310 can then be advanced via actuation of the probe 208 and inserted into a newly-unblocked sinus ostium 110. Additionally, a lumen within the probe 208 can be used to deliver therapeutic pharmaceutical agents, irrigation fluid, or other therapies directly into the maxillary sinus 106 (FIG. 1). The lumen can also house an actuation wire or electrical wires that can be used to power a therapy. Additional device controls can exist, such as fluidic port(s) 312 in the handle assembly 220 can provide attachment to pressure or fluid delivery applications.

A retail kit may also be packaged for consumer purchase. The kit can include one or both of a treatment and placement device 200 and a sinus ostium patency device 310, such as that described in commonly-owned Arcand, et al., U.S. patent application Ser. No. 12/837,224, entitled "IMPLANTABLE DEVICES FOR TREATMENT OF SINUSITIS," filed concurrently herewith, the entirety of which is incorporated herein by reference. The kit can also include a set of instructions for using the treatment and placement device or the patency device. In some examples, the kit includes one or more separate tools for withdrawing the sinus ostium patency device from an implanted position.

In operation, the second, distal portion 204 of the treatment and placement device 200 is inserted into position within the maxillary sinus 106 adjacent to the maxillary sinus ostium 110. Once the catheter 206 has been positioned, movement of the probe 208 in the proximal direction progressively or incrementally releases the probe's 208 preconfigured bias from within the catheter (see, e.g., FIG. 6). As the proximal movement of the probe 208 continues, the probe tip 210 gradually extends outward away from a longitudinal axis 216 of the catheter 206, as shown in FIG. 4B. By retrograde movement of the free tip 210 of the probe 208 alone or in simultaneous retrograde movement of the probe 208 and catheter 206 together, the probe tip 210 can be inserted into the maxillary sinus ostium 110.

Figure 4A:
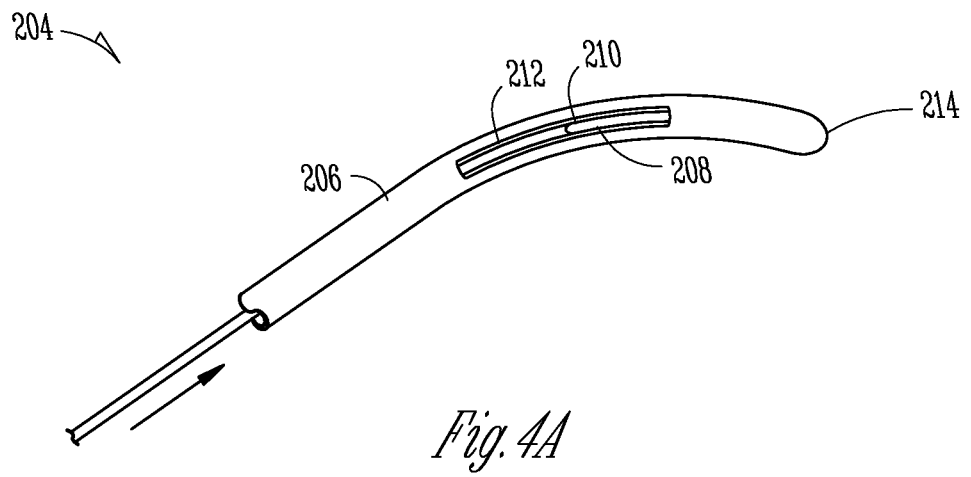
FIGS. 4A-4B illustrate side views of a distal portion of an example treatment and placement device, including the interplay between a hollow catheter and a nested probe, as constructed in accordance with at least one embodiment.
Figure 4B:
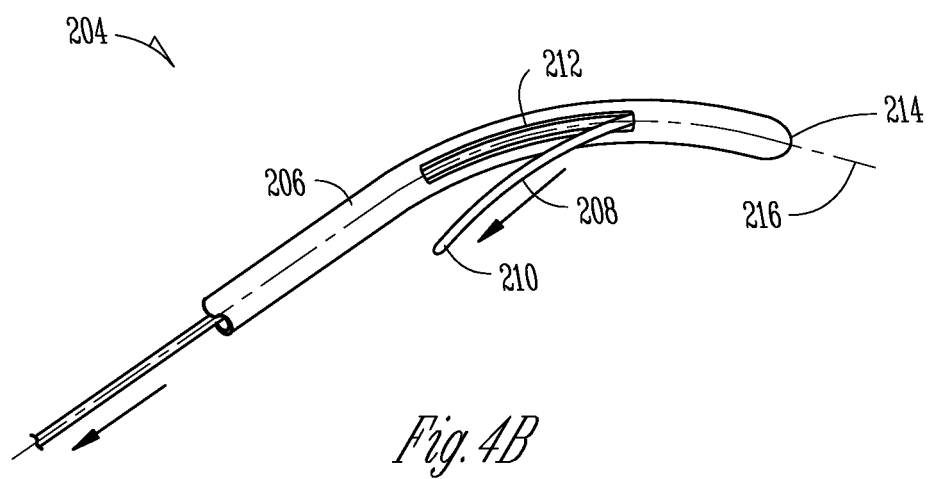

As shown in FIGS. 4A and 4B, the treatment and placement device 200 can comprise a portal 212 on a medial lateral surface portion of the catheter 206, in communication with a catheter lumen 218, and located proximal to a catheter distal end 214. In the example shown, the portal 212 is illustrated as an elongated channel or trough located in the catheter body through which the probe 208 can reside when deployed. Although illustrated as an elongated channel, the portal 212 can have a variety of shapes or configurations. For example, the portal 212 can be oval, or configured as a side portal through which a double-backed portion of the probe 208 can exit. An advantage associated with the elongated channel or trough portal 212 is that an arcuate configuration of the double-backed portion of the probe 208 can reside within the channel and cooperate with a generally arcuate distal catheter 206 configuration. In this way, the double-backed portion of the probe 208 can likewise have a generally arcuate configuration that can be maintained throughout the gradual outward biased extension affected by the deployment of the probe 208 from the catheter 206.

Figure 5A:
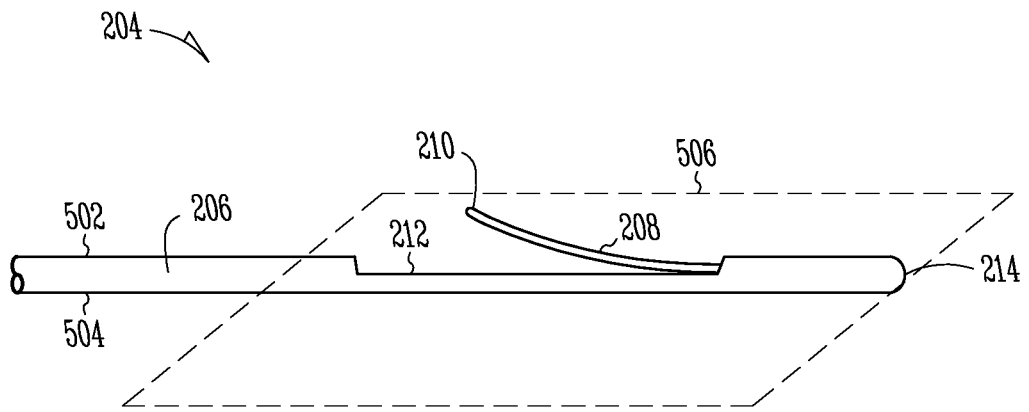
FIGS. 5A-5B illustrate side views of a distal portion of an example treatment and placement device, as viewed along a plane parallel to a flat device portion and toward the generally flat portion, as constructed in accordance with at least one embodiment.
Figure 5B:
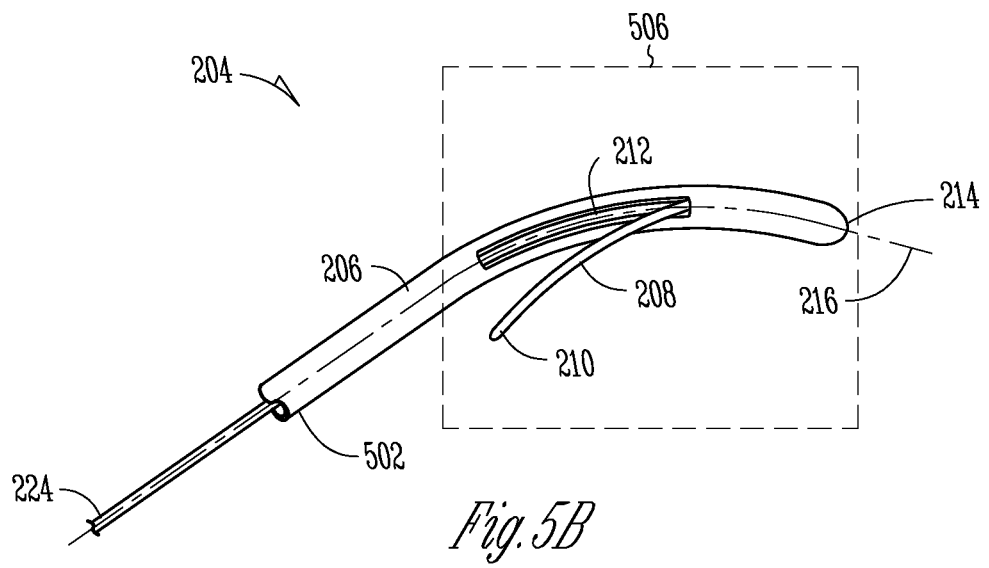

FIG. 5A is a side view of a second, distal portion 204 of an example treatment and placement device. In this example, a probe 208 is shown in a deployed position, as viewed along a plane 506 parallel to opposing flat sides 502, 504 of the device. FIG. 5B is also a side view of the second, distal portion 204 of the treatment and placement device. In this example, the probe 208 is shown in the deployed position, as viewed toward a flat side 502 of the device.

In various examples, a distal tip 214 of the catheter 206 is rounded and smooth to increase comfort and reduce trauma during device 200 positioning within a subject recipient. In some examples, a distal portion 204 of the device includes an elliptical, rectangular or ovoid flattened cross-section. In the example of FIGS. 5A and 5B, the distal portion 204 includes two opposing sides 502, 504 having generally flat surfaces.

The double-backed portion of the probe 208 can have a preformed arcuate configuration consistent with an arcuate configuration of the catheter 206. The double-backed portion of the probe 208 can be biased at a bend 602 (see, e.g., FIG. 6) to extend a probe tip 210 away from a longitudinal axis 216 of the catheter 206 at an angle 604 (FIG. 6) of about 90 degrees or less relative to a proximal portion of the axis 216. The angle 604 can be measured using the probe tip 210 relative to the vertex of the bend 602 and the general longitudinal axis 216 running between a proximal end of the catheter 206 and the bend 602. The angle 604 can vary based on the particular subject recipient's anatomical geometry. For example, the preferred probe 208 extension angle for a typical adult can be about 95 degrees or less. The preferred probe 208 extension angle for a child can be about 60 degrees or less.

Figure 6:
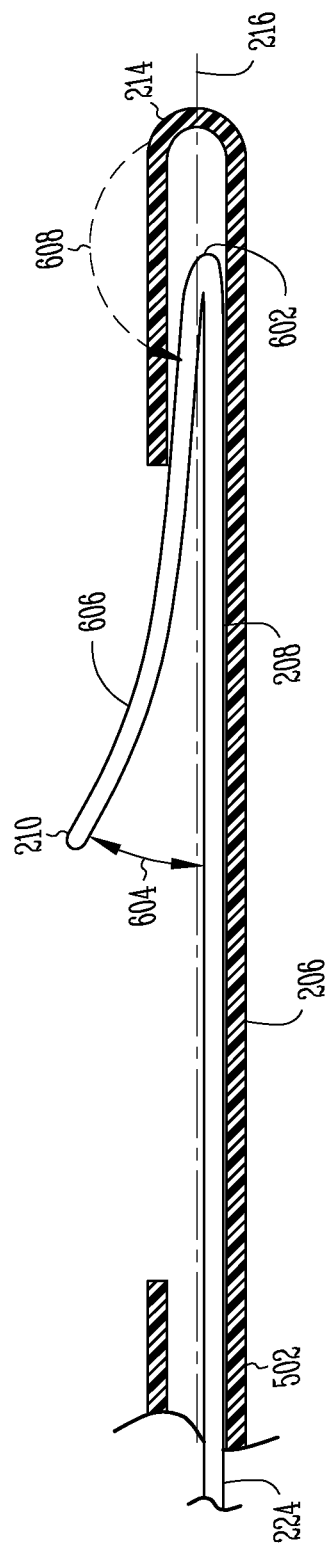
FIG. 6 illustrates a side, cross-sectional view of an example treatment and placement device, as constructed in accordance with at least one embodiment.

FIG. 6 illustrates a cross-sectional side view of a second, distal portion 204 of an example treatment and placement device. In this example, a probe 208 is shown in a deployed position, as viewed toward an edge of a generally flat side 502 of the device. When the probe 208 is deployed, a probe tip 210 extends away from a catheter 208, while remaining portions of the probe 208 remain nested within a lumen of the catheter 208. A double-backed portion 606 of the probe 208 created by the bend 602 can form an obtuse angle 608 between about 90 degrees and about 180 degrees relative to a distal portion of the longitudinal axis 216. The double-backed portion 606 of the probe 208 can be biased, as shown, at the bend 602 to extend the probe tip 210 away from a longitudinal catheter axis 216 to an angle 604 of about 90 degrees or less relative to a proximal portion of the longitudinal axis 216.

The preformed bend 602 and preformed extension bias of the probe 208 can be associated with operative advantages of the device. For example, the preformed bend 602 can reduce the likelihood of kinking, buckling, or other deformation of the probe 208, relative to "pushing" approaches, due to its "pulling" or retrograde movement approach. In addition, the preformed bend angle 604 of the probe 208 can allow for multiple direction movement using a single actuation force (e.g., proximal movement of a sliding switch can result in proximal and outward movement of the probe tip 210). Furthermore, the retrograde probe movement made possible by the bend 602 accounts for natural anatomical geometry to enhance positioning of the probe tip 210 into the ostium 110 (FIG. 1) of a subject recipient.

In various examples, the cross-sectional dimension (e.g., diameter or thickness) of the probe tip 210 is configured to accommodate the natural interior dimensions of the maxillary sinus ostium 110 to permit entry and movement within the sinus structure. In some examples, the outer diametrical dimension of the probe tip 210 can be about 5.0 mm or less, preferably between about 5.0 mm and about 0.5 mm, provided the structural integrity of the probe 208 needed for a desired function is not substantially compromised by its cross-sectional dimension.

Figure 7:
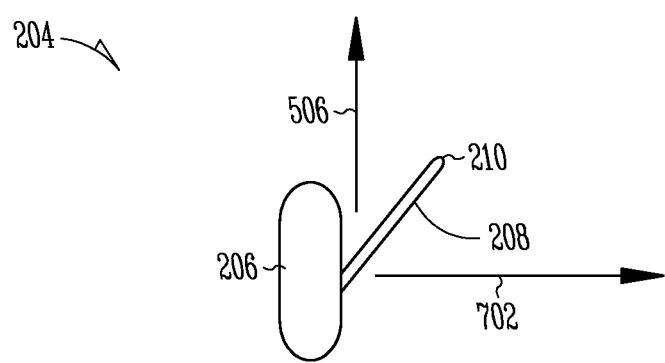
FIG. 7 illustrates an end view of a distal portion of an example treatment and placement device, as constructed in accordance with at least one embodiment.

FIG. 7 illustrates an end view of a distal portion 204 of an example treatment and placement device. In this example, a probe 208 is shown in a deployed position. In addition or in combination with the outward bias angle 604 (FIG. 6) relative to the longitudinal device axis 216, the bias movement of the probe 208 can be askew as opposed to a purely perpendicular directional movement relative to the catheter 206. Using reference plane 506 from FIGS. 5A and 5B, and a reference plane 702 perpendicular to plane 506, a probe tip 210 can be shown to have an askew outward bias deployed state which, in combination with the other device features disclosed herein, can be used to accommodate the natural geometry of the maxillary sinus by more precisely positioning the probe tip 210 in alignment with the maxillary sinus ostium.

Throughout this disclosure, the treatment and placement device 200 has been described herein as a device for accessing a maxillary sinus ostium and associated maxillary sinus. In many of these embodiments, the probe 208 extends in a direction substantially parallel to a lateral plane shared with an arcuate distal portion of the device. Alternatively, the teachings of the present device can be constructed and configured for accessing a frontal sinus and frontal sinus ostium, for example. For frontal sinus embodiments, the device can be constructed so that the probe 208 extends in a lateral direction perpendicular to a plane of the arcuate distal portion of the device to orient the probe 208 in an upward direction when positioned within the frontal sinus.

In various examples, such as to accommodate subject-varying maxillary sinus ostia and frontal sinus ostia geometries, the treatment and placement device 200 can be configured such the probe 208 can be directionally controlled by a physician caregiver. This directional control can include angular extension control of the probe 208 relative to the catheter 206, side extension control of the probe 208 from the catheter 206 (e.g., to accommodate left or right side sinus ostia) or retrograde movement control of the probe 208, among other directional options physician caregivers would like to select from to achieve better probe tip alignment with a desired ostium. It should be understood that the treatment and placement device 200 configurations discussed herein can be adjusted, as necessary, to accommodate left anatomical sinus uses in addition to right anatomical sinus uses. Illustrations in the drawings depicting a left or right side sinus use do not imply a limitation of the invention confining the device structure and configuration to the one particular anatomical side.

Experimental Example

Figure 8A:
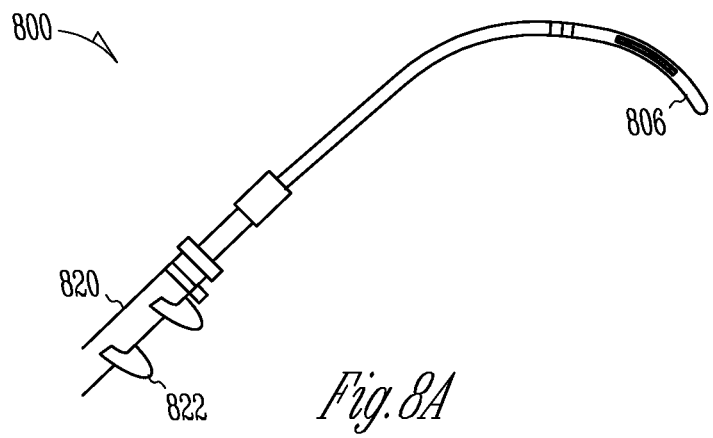
FIGS. 8A-8D illustrates an example experimental prototype of a present treatment and placement device.
Figure 8B:
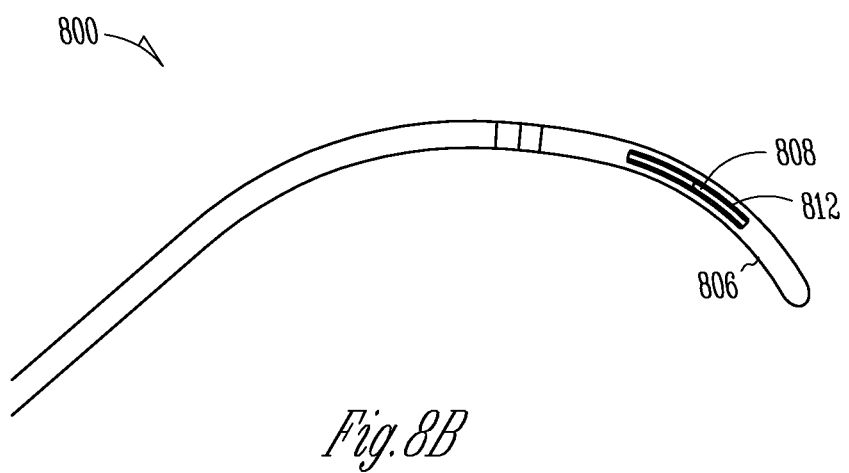
Figure 8C:
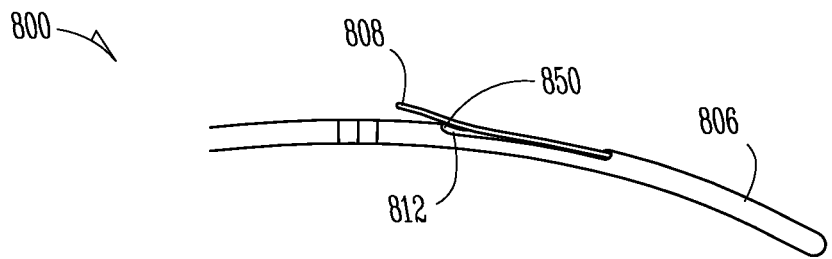
Figure 8D:
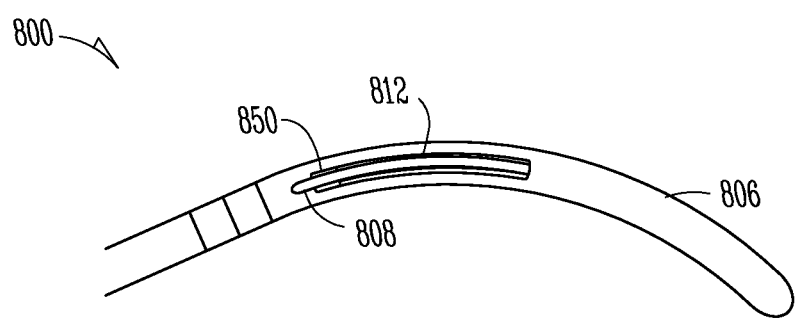

In order that the present treatment and placement device can be more fully understood, the example experimental prototype of FIGS. 8A-8D is given by way of illustration. In this example, the treatment and delivery device 800 includes a handle assembly 820 including a sliding switch 822 to actuate a probe 808 nested within a catheter 806. A distal end of the catheter 806 is sized and shaped to aid in positioning the device 800 within a nasal passageway. The distal end of the catheter 806 consists of a sleeve that is shaped with a non-circular cross-section to position itself under a middle turbinate. The sleeve of the catheter 806 houses the probe 808 used to gain access to a maxillary sinus ostium. The probe 808 exits via a portal 812, which is located near, but proximal, the distal end of the catheter 808. Additionally, a groove 850 proximal to the portal 812 was built into the catheter 808 to assist a probe tip 810 into the ostium and providing a backing to help push the probe tip 812 into the ostium. In this example, the groove 850 in the catheter 806 is directed such that the probe 808 exits laterally. FIGS. 8A-8B, in order, show an example advancement of the probe tip 810 from the catheter 806.

Closing Notes:

Treatment and placement devices, methods and kits which, when installed or used, access, aspire, dilate, insufflate, drain or deliver fluid medicaments to, or place a patency device within a sinus area, such as a maxillary sinus and a maxillary sinus ostium. A treatment and placement device can include a catheter that houses a probe, and optionally, a sinus ostium patency device. A tip of the probe is designed to exit from a lateral portal in the catheter, which is located proximal to a distal end of the device, by being pulled proximally or in a retrograde manner. This can allow the catheter to position the probe tip for access to a sinus ostium of interest, and easily allows the probe tip to be delivered from a posterior to anterior direction into the ostium. The probe that is housed in the catheter is double-backed so that its tip faces toward a proximal end of the device.

The overall catheter can be shaped to get the probe positioned alongside the ostium by providing the correct angle to enter the nostril and slide along the underside of a middle concha. The probe that exits the catheter can also be shaped so that it bends toward a lateral nasal wall (toward the ostium) and uses an uncinate process to aid in guiding the probe tip into the maxillary sinus ostium, for example. Optionally, a sinus ostium patency device can be attached to an end of the probe that exits the catheter and enters the ostium. Additionally, the probe, catheter, or both, can be used to deliver therapeutic pharmaceuticals or other therapies directly into the sinus of interest. A lumen of one of the probe or catheter can be used to house an actuation wire or electrical wires that can be used to power a therapy or release an implant mechanism. After delivery of the desired implants or therapy, the lumen can be retracted back into the catheter for easy removal.

Advantageously, the present treatment and placement devices, methods and kits are believed to lower the overall cost of sinus care and prevent long term health issues by, among other things, (a) reducing the dependence on systemic pharmaceuticals and other medications, (b) avoiding invasive, cutting-based procedures for patency device placement with an ostium, (c) providing an ease of use not previously seen before in the sinus access field, and/or (d) facilitating a blind (e.g., endoscope-less) device delivery procedure.

The above Detailed Description includes references to the accompanying drawings, which form a part of the Detailed Description. The drawings show, by way of illustration, specific embodiments in which the present treatment and placement devices, methods and kits can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" are used to refer to an amount that is nearly, almost, or in the vicinity of being equal to a stated amount. In this document, the terms "proximal" and "distal" are used to refer to a device component location relative to a caregiver user. For example, a proximal device location would be a location closer to the user of the device, whereas a distal portion location would be a location farther away from the user of the device, such as the device portions interacting with a subject recipient. In this document, the term "subject" is meant to include mammals, such as for human applications and veterinary applications. In this document, the phrases "structured to accommodate natural anatomical sinus cavity geometry," "structured to accommodate maxillary sinus geometry," or similar mean that the catheter and probe have dimensions (e.g., lengths and cross-sectional sizes) and configurations structured to accommodate anatomical geometry associated with the nasal passageway and sinus regions.

In the appended claims, the terms "including" and "in which" are used as the plain-English equivalents of the respective terms "comprising" and "wherein." Also, in the following claims, the terms "including" and "comprising" are open-ended, that is, a system, assembly, apparatus, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more features thereof) can be used in combination with each other. Other embodiments can be used, such as by one of ordinary skill in the art upon reviewing the above description. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. For instance, the treatment and placement devices, methods and kits disclosed herein can provide techniques for treatment of a frontal sinus, ethmoid sinus, or sphenoid sinus, in addition to a maxillary sinus. In one such example, the device can be structured and configured to access the frontal sinus ostium by orienting a terminal portion of the probe upward, and likewise be structured to accommodate the natural anatomical geometry within the sinus for the frontal sinus. Thus, the following claims are hereby incorporated into the Detailed Description, with each claim standing on its own as a separate embodiment. The scope of the invention should be determined with reference to the appended claims, along with the full scope of equivalents to which such claims are entitled.

The Abstract is provided to comply with 37 C.F.R. §1.72 (b), to allow the reader to quickly ascertain the nature of the technical disclosure. It is submitted with the understanding that it will not be used to interpret or limit the scope or meaning of the claims.

What is claimed is:

1. A device for accessing a sinus ostium, comprising:
a catheter extending from a proximal end to a distal end, a portion of the distal end includes an arcuate shaped housing, the catheter including a longitudinally-extending lumen and an intersecting side portal located proximal to the distal end; and
a probe including a first portion and a second portion separated by a preformed bend, which is adjacent to and consistent with the arcuate shaped housing, the first portion extending from a probe proximal end to the preformed bend and the second portion extending from the preformed bend in a direction toward the probe proximal end;
wherein the probe is at least partially nested within the arcuate shaped housing and the longitudinally-extending lumen and a portion of the probe is movable within the lumen such that a probe tip is advanceable out of the intersecting side portal and housing.

2. The device of claim 1, wherein the preformed bend forms an angle between about 90 degrees and about 180 degrees relative to an axis defined by the catheter distal end.

3. The device of claim 1, wherein the probe tip advances out of the intersecting side portal at an angle less than 90 degrees relative to a vertex at a distal end of the side portal and relative to an axis defined by the first portion of the probe at a superimposed position of the probe tip.

4. The device of claim 1, wherein the probe tip is configured to advance out of the intersecting side portal in a posterior to anterior direction.

5. The device of claim 1, wherein a distal portion of the catheter includes a groove, separate from and located proximal to the intersecting side portal, to support a portion of the probe.

6. The device of claim 1, wherein the probe is moveable within the longitudinally-extending lumen without movement of the catheter.

7. The device of claim 1, wherein the probe includes a tubular configuration and one or more openings at or near the probe tip.

8. The device of claim 1, further comprising an inflatable or expansible element coupled to the probe at or near the probe tip and in communication with a probe lumen.

9. The device of claim 1, wherein the catheter includes a combination of a semi-rigid internal material and a softer, more pliable exterior material.

10. A kit comprising:
    the device according to claim 1; and
    a set of instructions for using the device to treat an ostium associated with a maxillary sinus.

11. The kit of claim 10, further comprising a sinus ostium patency device for maintaining a sinus ostium in an open state while maintaining a track of uncovered cilia within the ostium.

* * * * *

UNITED STATES PATENT AND TRADEMARK OFFICE
CERTIFICATE OF CORRECTION

PATENT NO. : 8,435,261 B2  
APPLICATION NO. : 12/837256  
DATED : May 7, 2013  
INVENTOR(S) : Arcand et al.

Page 1 of 1

It is certified that error appears in the above-identified patent and that said Letters Patent is hereby corrected as shown below:

On the Title page, in column 1, under "(73) Assignee", line 2, after "Paul", insert --, MN (US)--, therefor On the Title page, in column 2, under "Other Publications", line 1, delete ""Internatonal" and insert --"International--, therefor In the Specification:

In column 1, line 9, delete "OSTIUM,"," and insert --OSTIUM,"--, therefor

In column 4, line 19, delete "FIG." and insert --FIGS.--, therefor

In column 10, line 15, after "such", insert --that--, therefor

In the Claims:

In column 12, line 54, in Claim 1, delete "end;" and insert --end,--, therefor

Signed and Sealed this  
Twenty-fourth Day of September, 2013

Teresa Stanek Rea  
*Deputy Director of the United States Patent and Trademark Office*